United States Patent [19]
Greengarg

[11] Patent Number: 5,318,507
[45] Date of Patent: Jun. 7, 1994

[54] DETACHABLE BACK, BELT, APRON, METHOD

[76] Inventor: Gerson M. Greengarg, 17063 Ryton La., Boca Raton, Fla. 33496

[21] Appl. No.: 907,832

[22] Filed: Jul. 2, 1992

[51] Int. Cl.⁵ ............................................. N61F 5/00
[52] U.S. Cl. .................................. 602/19; 2/48
[58] Field of Search .............. 602/19; 128/96.1, 99.1, 128/100.1, 101.1, 874, 875; 2/48, 51, 102

[56] References Cited

U.S. PATENT DOCUMENTS

| | | | |
|---|---|---|---|
| 1,739,112 | 12/1929 | Wisbrod | 2/102 X |
| 2,076,076 | 4/1937 | Dunlap | 2/102 X |
| 3,611,438 | 10/1971 | Gregg et al. | 2/51 |
| 3,641,997 | 2/1972 | Posey, Jr. | 128/874 X |
| 5,040,524 | 8/1991 | Votel et al. | 602/19 |
| 5,148,549 | 9/1992 | Sydor | 2/51 X |
| 5,188,586 | 2/1993 | Castel et al. | 602/19 |

Primary Examiner—Richard J. Apley
Assistant Examiner—Linda C. M. Dvorak
Attorney, Agent, or Firm—Jack E. Dominik

[57] ABSTRACT

Various combinations of a detachable back belt, an apron, and a lifting belt which is a direct body engaging member with ends that are closed underneath an apron is disclosed. The method of the invention is directed to applying the combination of apron, lifting belt, suspenders, and detachable back belt to the user by first putting on the apron. Thereafter, the lifting belt is slipped under the apron, the suspenders secured over the shoulders, and the suspenders optionally adjusted at that time for the short chested or long torso person.

3 Claims, 5 Drawing Sheets

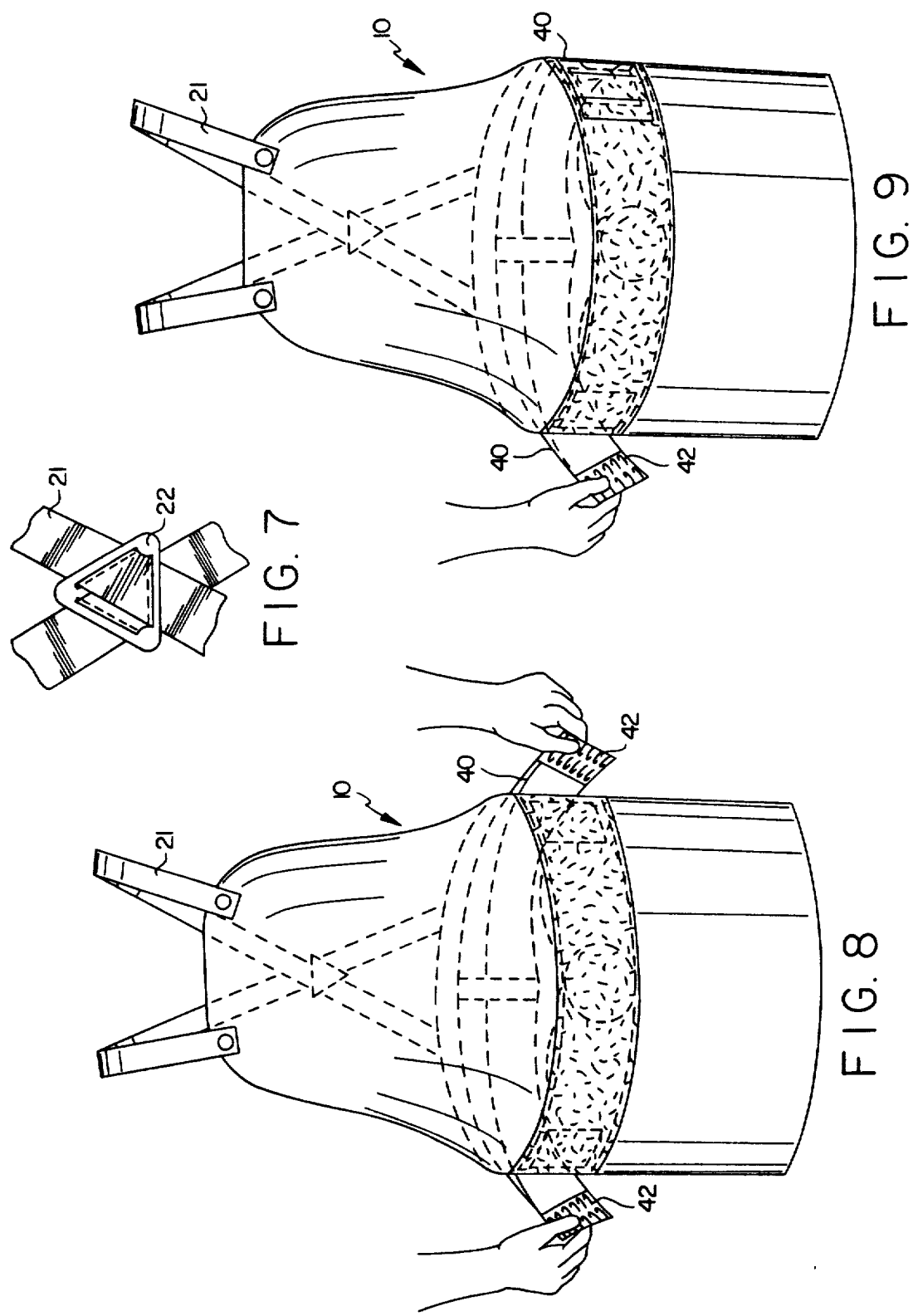

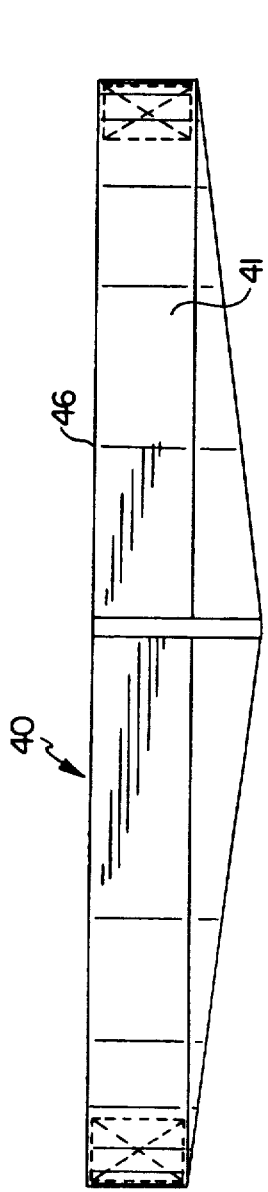
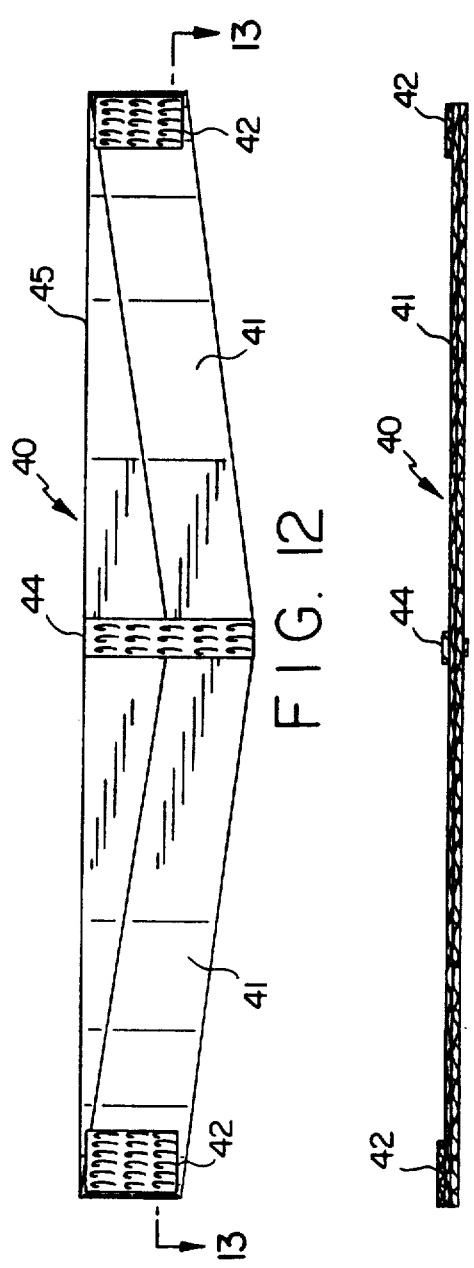
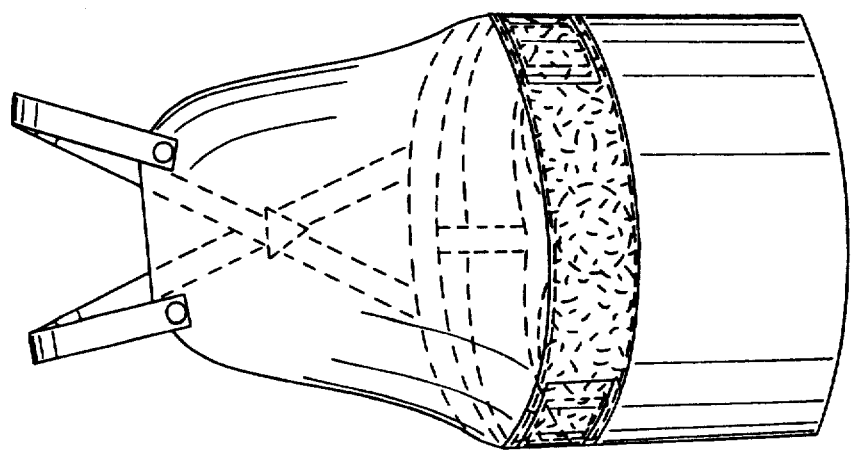

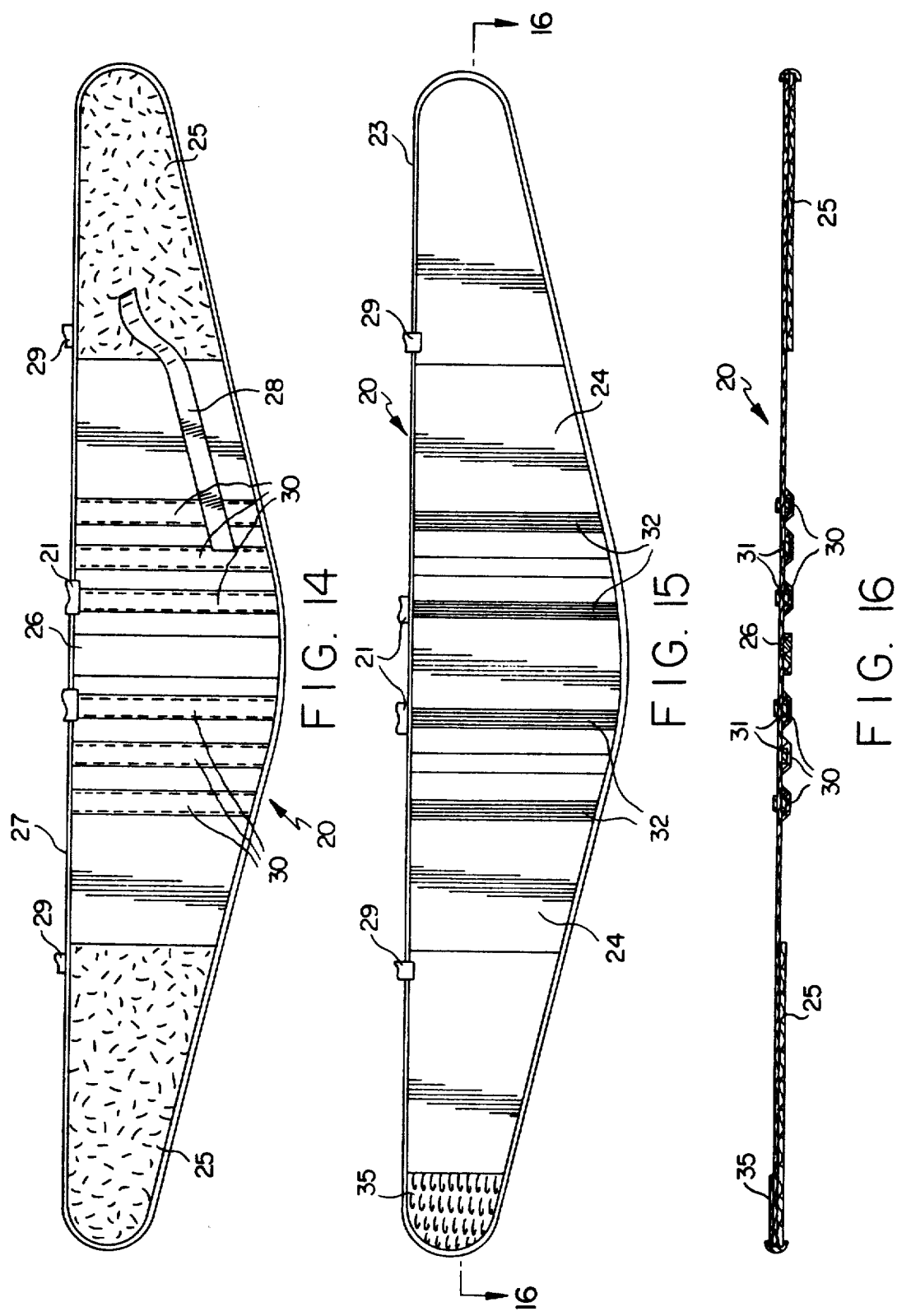

DETACHABLE BACK, BELT, APRON, METHOD

FIELD OF THE INVENTION

The present invention relates to lifting belt assemblies of the type typically worn by warehouse men, nurses, factory workers and the like where lifting is a common part of the duties and awkward positions should be anticipated.

SUMMARY OF THE PRIOR ART

The prior art abounds with elastic belts or leather bands secured around the lower lumbar region of the back with flat supports on the back portion and a detachable front portion for securing the same. Aprons are often worn by the person using the belt. The apron may be worn outside the belt, or sometimes inside the belt.

In many environments the aprons become soiled to the point where they cannot be cleansed, they are literally discarded. In such an environment, it is to be anticipated that the back of the belt of the user may very well become soiled. Accordingly, it is highly desirable to create an assembly of apron, lifting belt and detachable back belt to the end that the apron can be discarded, optionally the back belt can be discarded, but the underlying lifting belt may be the subject of ongoing use by the wearer.

SUMMARY OF THE INVENTION

The present invention is directed to various combinations of a detachable back belt, an apron, and a lifting belt which is a direct body engaging member with ends that are closed underneath an apron. The lifting belt has vertical stays, and an elastic body portion with belt loops to prevent the same from riding up the torso of the user. The apron is formed with the traditional lower pocket sections, and has means for securing to the suspenders which are an extension of the lifting belt. The front of the apron is provided with a loop-hook engaging section in the shape of a transverse strap. Finally, a detachable back belt secures to the rear portion of the underlying lifting belt and wraps around the same to finalize the securement by overlapping the already assembled overlapping end portions of the lifting belt and securing the ends to the apron transverse strap. A lifting belt hook central engaging member on the detachable belt engages the back of the lifting belt. The method of the invention is directed to applying the combination of apron, lifting belt, suspenders, and detachable back belt to the user by first putting on the apron. Thereafter, the lifting belt is slipped under the apron, the suspenders secured over the shoulders, and the suspenders optionally adjusted at that time for the short chested or long torso person. Subsequently, the underlying lifting belt ends are overlappingly engaged to each other. Thereafter, the detachable back is secured to the lifting belt and apron. Finally, just before using, the wearer will tighten the ends of the lifting belt, and then pull the ends of the detachable back belt snugly towards each other and overlie them on the loop portion of the front of the apron. The underneath portion of the apron and its lateral edges hook members engage the underlying lifting belt loop ends prior to the detachable back ends being secured over the front of the apron.

It is a principal object of the present invention to provide for a disposable apron to be used in combination with a lifting belt. A related and important object of the invention is to add to the combination of disposal apron and lifting a detachable back belt portion which assists in securing the lifting belt from a standpoint of utility, and yet can be thrown away if it becomes soiled to the degree of the apron while retaining the lifting belt. Since the cost of the replaceable apron and replaceable detachable back belt is perhaps one-third of the total cost of the original package, this occasions a savings in annual usage in those places where the aprons and/or detachable back belts must be discarded as often as once every three months.

Still another object of the present invention is to provide for continuity and overlapping relationship between all of the members including apron, lifting belt, detachable back belt, and suspenders to the end that a coordinated securement is achieved by the user as dictated by the relationship of the elements of the three principle elements along with the suspenders.

An additional objective of the present invention is to provide a stand alone apron with an elastic neck band for applications where a lifting belt will not be worn, but the apron can serve as a part of inventory adaptable for use with the lifting belt or without.

Yet another object of the present invention is to provide a lifting belt with a detachable belt which can be used without the use of an apron.

BRIEF DESCRIPTION OF THE DRAWINGS

The present invention will be better understood as taken in conjunction with the accompanying illustrative drawings, in which:

FIG. 7 is a partially broken view of the adjustment triangle used where the suspenders overlap each other in the back portion for accommodating various sizes of users;

FIG. 8 is a partially diagrammatic view illustrating the application of the detachable back belt to the front loop band of the apron;

FIG. 9 is a further sequential view from that shown in FIG. 8 illustrating the second hook inner end of the detachable belt being applied to the loop band in the front of the apron:

FIG. 10 is a final view illustrating the two ends of the detachable back secured to the front loop portion of the apron ready for lifting or for readjustment prior to lifting;

FIG. 11 is an outside view of the detachable back belt;

FIG. 12 is a wearer side plan view of the detachable back belt;

FIG. 13 is a transverse sectional view of the detachable back belt taken along section lines 13—13 of FIG. 12;

FIG. 14 is an outer face view of the lifting belt;

FIG. 15 is the wearer side or front elevation of the lifting belt showing the hook end at the left-hand portion of FIG. 15; and FIG. 16 is a transverse sectional view of the lifting belt taken along section lines 16—16 of FIG. 15.

DESCRIPTION OF PREFERRED EMBODIMENTS

Disposable Apron

Figure 1:
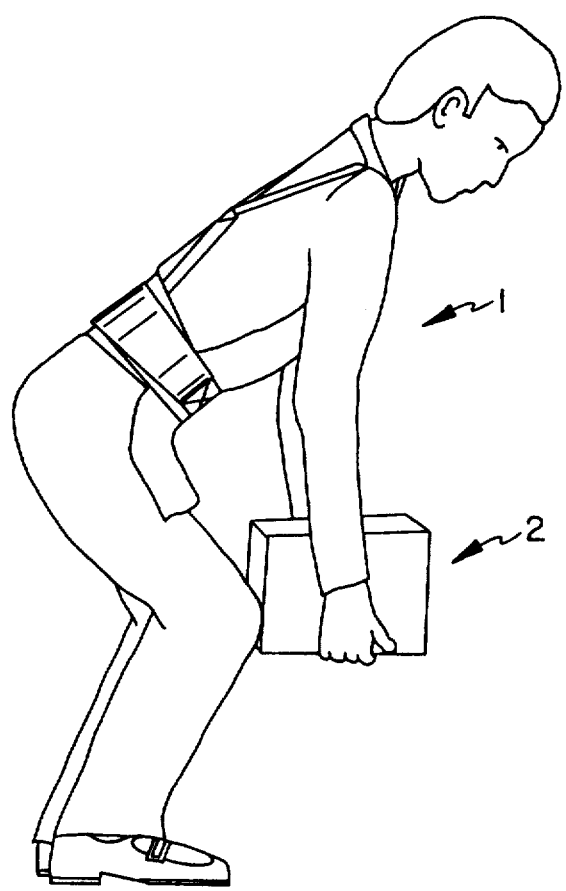
FIG. 1 shows a side elevation of a warehouse man lifting a load wearing an assembly illustrative of all aspects of the present invention.
Figure 2:
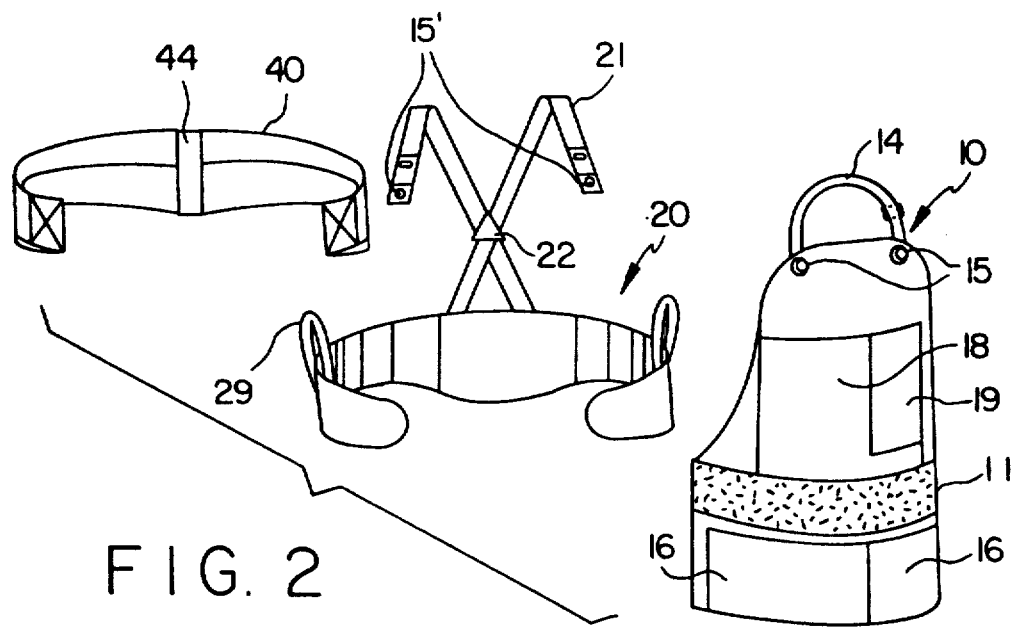
FIG. 2 is a partially diagrammatic view showing the apron, lifting belt, and detachable back belt elements illustrative of the present invention.

The disposable apron 10 illustrative of the present invention is shown on the warehouse man 1 of FIG. 1, and in diagrammatic partially perspective view at the right-hand portion of FIG. 2.

The underlying lifting belt 20 is shown in the middle portion of FIG. 2. It is provided with suspenders 21 and an adjustable triangle 22 where the suspender bands cross over. It has snap fasteners 15' for securing to the male fasteners 15 of the apron 10.

Finally, the entire assembly is completed by use of the detachable back 40, the central portion of which has a hook portion which engages the loop portion back of the lifting belt 20, and underlying hook elements at each end which overlappingly engage the loop band 11 of the apron 10. Where hook and loop are referred to they are removably secured opposite members. The reverse order of loop and hook is also contemplated and in addition any releasably secured structure in which both elements are the same.

The Apron

Figure 3:
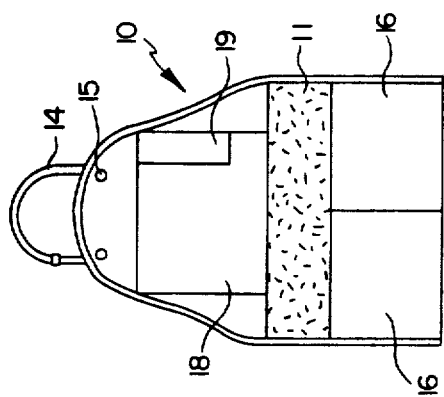
FIG. 3 is a plan view of the apron.
Figure 4:
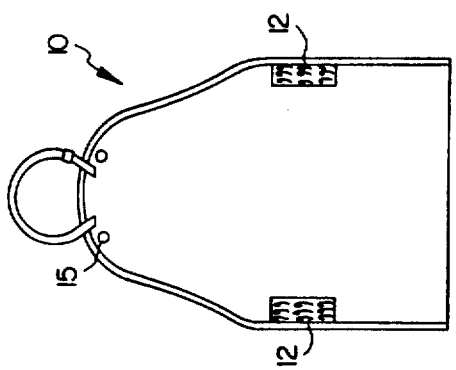
FIG. 4 is a plan view of the rear or wearer side of the apron of FIG. 3.

The stand alone disposal apron 10 is best shown in FIGS. 3 and 4. There it will be seen that there is a preferred cotton body portion which has a transverse loop band 11 crossing the entire front portion. While the loop band 11 could be a hook band 11, the outer loops are less likely to abrade the arms of the wearer and less likely to entrap small particles of scrap. Beneath the loop band 11 are a pair of bottom pockets 16. An elastic loop 14 is provided at the upper portion of the apron with an adjustable feature for length of the user, neck size, and the like. Detachable male snaps 15 are provided to engage the ends of the suspenders. The traditional upper pouch 18 and pencil pocket 19 are provided in the front portion of the apron. The underneath portion or wearer side of the apron is best illustrated in FIG. 4 where the elements are the same as those shown in FIG. 3 with the exception of the hook strips 12 which are provided to engage the loop end portions of the lifting belt 20 as will be described hereinafter. In addition, the suspenders 21 are provided with an adjustable triangle 22 as shown in FIG. 7 which permits raising and lowering the intersection of the two members of the suspender pair 21.

The Lifting Belt

Turning now to FIGS. 14–16, it will be seen that the lifting belt 20 has a pair of permanently secured suspenders 21 secured to its upper edge. The back engaging face 23 is the one shown in FIG. 14. The body of the lifting belt 20 is formed of a Spandex-like foundation 24. Overlapping the two ends of the outer face 27 are loop end sections 25. To be noted is the non-elastic anchor band 28 which is secured at one end to one of the pockets 30 and at the other end to an adjacent loop end portion 25. The purpose of the non-elastic anchor band 28 is to prevent expanding or stretching the belt beyond its practical limits. Finally, belt loops 29 are provided at the beginning portion of the end loop sections 25 which have appropriate hooks in order to go over the belt of the wearer and then secure back again on the outer loop section 25.

Further to be noted particularly as in FIG. 16 provision is made for four of the pockets 30 to contain flexible stays 31. Optional rubberized stitching 32 is provided on the back engaging face to cooperate with the belt loops 29 to further secure the lifting belt 40 to the user and not ride up the torso.

The Detachable Back Belt

The detachable back belt 40 is best shown in FIGS. 11–13. There it will be seen that it is comprised of overlapping elastic band members 41 and terminates on the body side with a pair of apron engaging hook ends 42. The body side 45 also has a central lifting belt back loop-hook engaging element 44. The outer portion of the detachable belt 46 has no loop or hook elements, as shown in FIG. 11. Thus, it is less vulnerable to soil than the apron which must have the loop elements in front.

The Method

Figure 6:
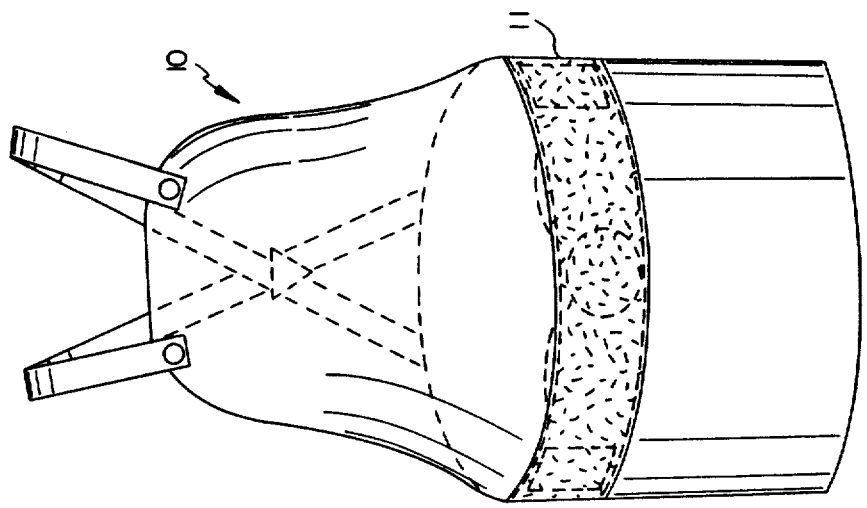
FIG. 6 is a further sequential view from that of FIG. 5 showing the apron after the lifting belt has been secured therebeneath.
Figure 5:
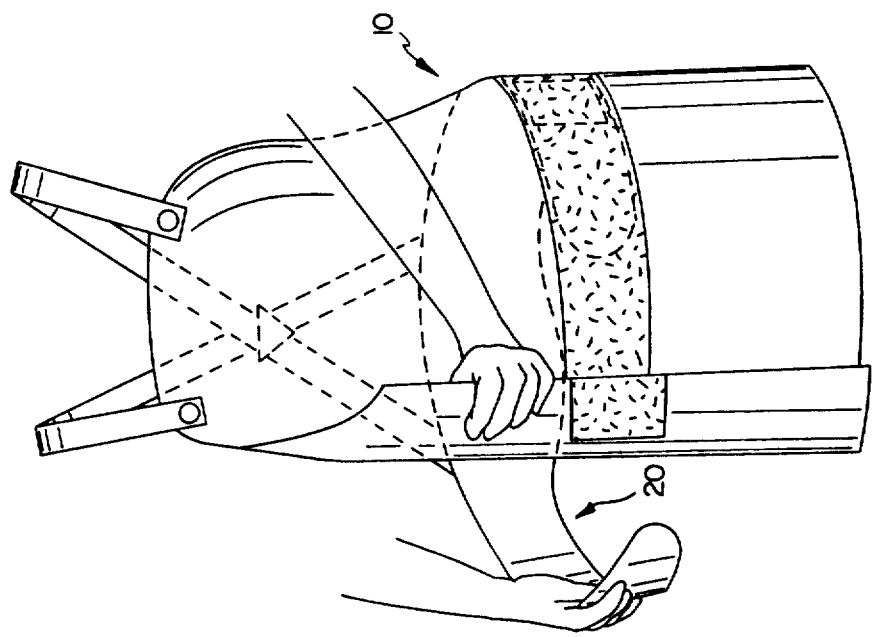
FIG. 5 is a partially diagrammatic view illustrating the application of the lifting belt after the apron has been placed over the wearer.

The method of the present invention is illustrated by the sequences of applying the same in FIGS. 5 and 6, and 8–10. The apron 10 which is a stand alone apron can be used without the lifting belt 20 or the detachable belt 40. On the other hand, when the assembly is to be worn in its entirety, the apron 10 is first desirably put on by the user which includes inserting his head underneath the elastic neck band 14. Once the apron 10 is on, the lifting belt 20 is secured beneath the apron 10 with its one overlapping hook portion from the wearer side overlapping the opposite of the two end loop portions. The belt loops 29 are then applied to the belt of the user, and the suspenders 21 secured by means of snaps 15' to the male snaps 15 of the apron 10. The early positioning of the apron and then positioning the lifting belt 20 is shown in FIG. 5. Thereafter, as shown in FIG. 6, the lifting belt is secured underneath the apron 10 and the apron loop band 11 is exposed throughout the entire frontal portion of the apron 10. Some may find it easier to don the lifting belt before the apron 10. Thereafter the user is ready to apply the detachable back belt 40 as illustrated in FIG. 8. The detachable back belt 40 has two inner hook ends 42 which are secured to the outer loop band 11 of the apron 10, first the one side as shown in FIG. 9, with the other side loop portion 42 in the hand of the user as shown in FIG. 9, and finally both ends are secured as illustrated in FIG. 10.

Although particular embodiments of the invention have been shown and described in full here, there is no intention to thereby limit the invention to the details of such embodiments. On the contrary, the intention is to cover all modifications, alternatives, embodiments, usages and equivalents as fall within the spirit and scope of the present invention, specification and appended claims.

What is claimed is:

1. A combination of an independent detachable back belt having apron engaging ends, an independent lifting belt, and an independent apron combination, comprising, in combination, said independent lifting belt having stays engaging the lower lumbar portion of the back and ends which are overlappingly releasably secured to each other and having outside securement portions for receiving further detachable secured members, an apron portion having upper and lower ends with a mid-band of releasably securable material for securing a detachable wrap-around apron engaging member, suspender securing means at the upper portion of the apron for receiving suspenders secured to the lifting belt, and a detachable apron engaging back belt having central means for releasably securing the detachable back belt to the underlying lifting belt and also having apron engaging end members for overlapping securement to the releasably securable midband of the apron.

2. A method of securing an independent lifting belt having suspenders, independent apron, and an independent detachable back belt having apron engaging ends to a person for purposes of assisting in lifting loads in which the lifting has on its inner portion of the ends a releasably securable material, and a releasably securable member on the opposed portion of one of the ends; and in which the apron has a mid band of releasably securable material across the front, and a releasably securable portion underneath the ends of the band portions on the body side of the apron; and a detachable back belt having a body and apron engaging releasably securable members underneath the two outer ends comprising the steps of:

positioning the lifting belt in place on the user by overlapping the ends against each other and engaging the suspenders, positioning the apron over the user and securing the inner releasably securable portions to the outer exposed releasably securable portions of the lifting belt, and securing the entire combination by wrapping the detachable belt around the user with its two inner releasably securable end portions overlapping the center loop band portion of the apron.

3. A method of securing a combination of three independent elements which are a lifting belt, an apron and detachable back belt to a person for purposes of assisting in lifting loads n which the lifting belt has on its inner portion ends of releasably securable material, and a releasably securable member on the opposed portion of one of said ends; a securable portion underneath the ends of the band portions on the body side of the apron; and a detachable back belt having a body and releasably securable members underneath the two outer apron engaging ends comprising the steps of:

positioning the lifting belt in place on the user and then overlapping the ends against each other, positioning the apron over the user and securing the inner releasably securable portions to the outer exposed releasably securable portions of the lifting belt, securing the suspenders attached to the lifting belt by traversing the shoulders, and securing the entire combination by wrapping the detachable back belt around the user with its two releasably securable portions overlapping the center releasably securable band portion of the apron.

* * * * *

UNITED STATES PATENT AND TRADEMARK OFFICE
CERTIFICATE OF CORRECTION

PATENT NO. : 5,318,507
DATED : June 7, 1994
INVENTOR(S) : Gerson M. Greenbarg

It is certified that error appears in the above-indentified patent and that said Letters Patent is hereby corrected as shown below:

On the title page:

Item [76] change Gerson M. Greengarg to Gerson M. Greenbarg

Signed and Sealed this

Eleventh Day of October, 1994

Attest:

BRUCE LEHMAN

*Attesting Officer*   *Commissioner of Patents and Trademarks*